United States Patent [19]
Haber et al.

[11] Patent Number: 4,846,808
[45] Date of Patent: Jul. 11, 1989

[54] SAFETY SYRINGE HAVING A NEEDLE TO BE RETRACTED AND CANTED WITHIN A PROTECTIVE SLEEVE

[75] Inventors: Terry M. Haber, Lake Forest; Clark B. Foster, El Toro, both of Calif.

[73] Assignee: Habley Medical Technology Corporation, Laguna Hills, Calif.

[21] Appl. No.: 156,531

[22] Filed: Feb. 16, 1988

[51] Int. Cl.$^4$ ............................................... A61M 5/32
[52] U.S. Cl. ..................................... 604/195; 128/763
[58] Field of Search ............... 604/192, 194, 195, 196, 604/197, 198, 263, 187; 128/763, 764, 765

[56] References Cited

U.S. PATENT DOCUMENTS 4,592,744  6/1986  Jagger et al. ........................ 604/192

Primary Examiner—John D. Yasko
Attorney, Agent, or Firm—Morland C. Fischer

[57] ABSTRACT

A shielded safety syringe comprising a cylindrical outer protective sleeve, a cylindrical inner needle carrier movable axially through the outer sleeve, and a double-ended hypodermic needle retained at a distal end of the needle carrier and movable with the carrier through the sleeve. A movement of the inner needle carrier through the outer protective sleeve corresponding causes the needle to be relocated from an axially extended position, at which to make a veni puncture through a patient's tissue, to a retracted position, at which the needle is completely surrounded and shielded by the outer sleeve to permit a safe handling and disposal of the syringe. A portion of the distal end of the needle carrier at which the needle is retained is pivotally connected to the needle carrier. When the needle is located in the retracted position, said distal end portion may be rotated and the needle thereby canted toward the outer sleeve to prevent both access to the needle and the return of the needle to the axially extended position, whereby to avoid an accidental needle strike and the spread of a contagious and, possibly life threatening, disease.

20 Claims, 1 Drawing Sheet

SAFETY SYRINGE HAVING A NEEDLE TO BE RETRACTED AND CANTED WITHIN A PROTECTIVE SLEEVE

BACKGROUND OF THE INVENTION

1. Field of the Invention

This invention relates to a shielded safety syringe having an outer protective sleeve and a retractable, double-ended needle which is moved through the outer sleeve between axially extended and retracted positions. Means are provided for canting the needle at the retracted position to prevent both access to and return of the needle to the axially extended position.

2. Prior Art

Syringes are used for a variety of purposes. By way of example, the syringe may be used for vacuum tube phlebotomy, where one or more samples of a patient's blood are successively drawn into respective evacuated blood collection tubes by way of a double-ended hypodermic needle cannula. Such a syringe may be used to treat a patient having a communicatable disease. Prior to disposal of the syringe, the hypodermic needle is sometimes broken to prevent reuse. Health care workers are especially susceptible to accidental and potentially infectious needle strikes due to the careless handling or breaking of the needle and disposing of the syringe after use. The resulting mini-accidents caused by an accidental needle strike typically requires a blood test for such diseases as AIDS and hepatitis. The corresponding cost and inefficiency of testing health care workers who have received an inadvertent needle strike result in considerable waste, which may be particularly to a health care facility which is striving for economy.

The following U.S. patent applications, which are or will be assigned to the assignee of the instant patent application, relate, respectively, to a shielded safety syringe and to a means for canting a single-ended needle at the interior of a hollow cylinder: U.S. application Ser. No. 118,745 filed Nov. 9, 1987 and U.S. application Ser. No. 51,392 filed May 19, 1987.

SUMMARY OF THE INVENTION

In general terms, a shielded safety syringe is disclosed comprising a cylindrical outer protective sleeve, a cylindrical inner needle carrier movable axially through the sleeve, and a double-ended hypodermic needle supported at a distal end of the needle carrier, such that the needle is aligned coaxially with respect to the outer sleeve and the inner carrier. The needle communicates with an evacuated blood collection tube at the interior of the outer sleeve. A position control button projects from the needle carrier and is received within and slideable through an axially extending guide channel which is formed in the outer sleeve. Proximal and distal locking detents are formed at opposite ends of the guide channel in which the position control button is received and locked to retain the needle carrier, and the needle supported thereby, at relatively proximal or distal positions relative to the outer sleeve.

A portion of the distal end of the inner needle carrier at which the needle is retained is pivotally connected to the needle carrier. That is, one end of said distal end portion is hingedly connected to the needle carrier and the other end is detachably connected to the carrier, such that the distal end portion may be rotated and the needle thereby canted toward the outer sleeve. A catch projects from the distal end portion at which the needle is retained and is received in and slideable through an axially extending catch slot which is formed in the outer sleeve. The guide channel and catch slot are arranged in parallel alignment with one another, with the guide channel having a longer length than the catch slot. Accordingly, the axial movement of the position control button through the guide channel causes the corresponding axial movements of the inner needle carrier through the outer sleeve and the catch through the catch slot.

In operation, the position control button is moved from the distal locking detent of the guide channel to the proximal locking detent to cause a corresponding movement of the inner needle carrier proximally through the outer sleeve and a relocation of the needle from an axially extended position relative to the outer sleeve, at which to make a veni puncture through the tissue of a patient and thereby obtain a blood sample, to a retracted position, where the needle is completely surrounded and shielded by the outer sleeve. However, inasmuch as the catch slot is shorter than the guide channel, the catch will be engaged and blocked by the end of the catch slot before the position control button is received in the proximal locking detent of the guide channel. Therefore, as the needle carrier continues to move proximally through the outer sleeve for relocating the needle to the retracted position, the distal end portion of the needle carrier at which the needle is retained will be rotated, such that the needle is canted towards and bent against the outer sleeve. Accordingly, access to and reuse of the needle is prohibited. Moreover, with the needle canted and the position control button received within the proximal locking detent, redundant locking means are provided to prevent a return of the needle to the axially extended position, whereby to avoid an accidental needle strike and the spread of a contagious and, possibly life threatening, disease.

DESCRIPTION OF THE PREFERRED EMBODIMENTS

Figure 1:
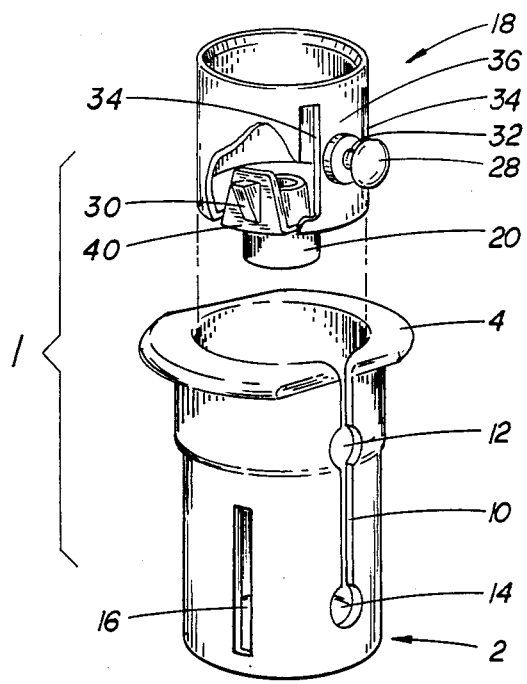
FIG. 1 illustrates an exploded view of the safety syringe which forms the present invention.

The shielded safety syringe which forms the present invention is now disclosed while referring to the drawings. FIG.1 shows an exploded view of the syringe 1 which includes a hollow, cylindrical (e.g. molded plastic) outer protective sleeve 2 having an open proximal end and a substantially closed distal end. A flange 4 extends around the open proximal end to facilitate the handling and operation of syringe 1. An opening 6 (best shown in FIGS. 4 and 5) is formed in the distal end of outer sleeve 2 to accommodate the neck of the soon to be described inner needle carrier 18 (best shown in FIG. 4), whereby a double-ended hypodermic needle cannula 8 can be relocated to an axially advanced position relative to sleeve 2 at which to make a veni puncture through the skin of a patient.

An axially extending guide channel 10 is formed through one side of the outer sleeve 2. Guide channel 10 includes coextensively formed proximal and distal locking detents 12 and 14. The diameters of locking detents 12 and 14 are larger than the width of guide channel 10. An axially extending catch slot 16 is formed through another side of outer sleeve 2, such that the channel 10 and slot 16 are arranged in parallel alignment with one another. Catch slot 16 extends from adjacent the distal end to approximately the mid-point of outer sleeve 2, such that guide channel 10 has a longer length than catch slot 16. The functions of guide channel 10 and catch slot 16 will be described in greater detail hereinafter.

Safety syringe 1 also includes a hollow, cylindrical (e.g. flexible molded plastic) inner needle carrier 18 having an open proximal end and a substantially closed distal end. When in the assembled relationship (e.g. of FIG. 4), needle carrier 18 is adapted to be received within and coaxially aligned with outer sleeve 2 so as to be moved axially therethrough.

Figure 2:
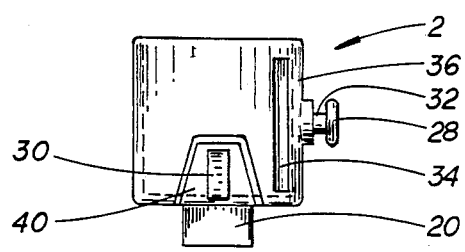
FIG. 2 is a front plan view of an inner needle carrier which forms the safety syringe of FIG. 1.
Figure 3:
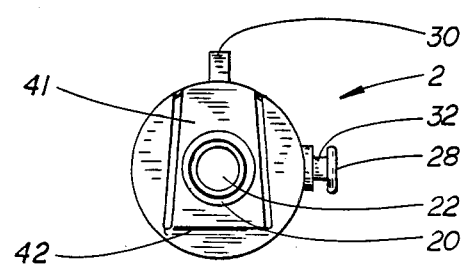
FIG. 3 is a bottom view of the needle carrier of FIG. 2.
Figure 4:
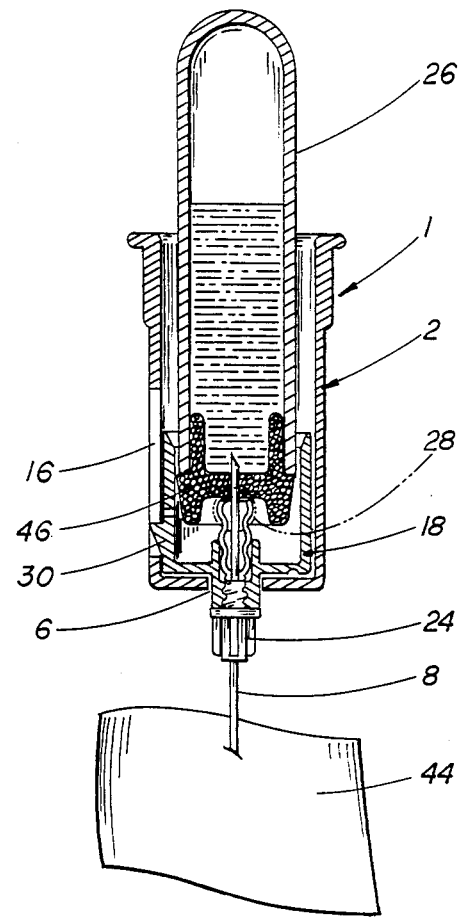
FIG. 4 shows the safety syringe in an assembled configuration with a hypodermic needle in an axially advanced position for making a veni puncture through a patient's skin to collect a blood sample.
Figure 5:
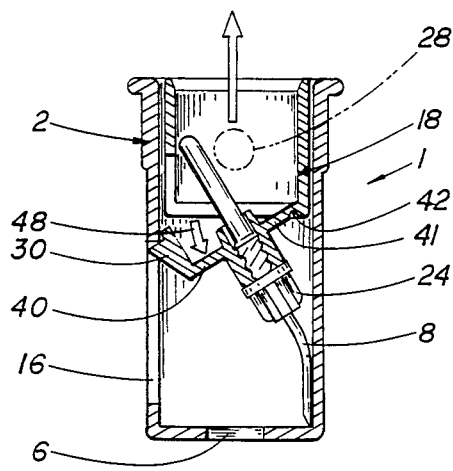
FIG. 5 shows the safety syringe with the hypodermic needle relocated to a retracted position so as to be canted towards and bent against an outer sleeve which forms the safety syringe of FIG. 1.

Referring concurrently to FIGS. 1-3 of the drawings, needle carrier 18 includes a distally extending, screw-threaded neck 20 which surrounds a relatively small opening 22 formed in the distal end of needle carrier 18. The opening 22 is sized to receive a screw-threaded hub (designated 24 in FIG. 4). Hub 24 is bonded (e.g. molded) to a conventional double-ended hypodermic needle cannula 8. In the assembled relationship (of FIG. 4), the screw-threaded hub 24 is mated to the screw-threaded neck 20 of needle carrier 18, such that needle 8 is retained at the distal end of the needle carrier in coaxial alignment with the outer sleeve 2 and the inner carrier 18. Accordingly, needle 8 is movable axially with inner needle carrier 18 through the outer sleeve 2 between an axially extended position (as illustrated in FIG. 4), at which to extend outwardly past the distal opening 6 in outer sleeve 2 to make a veni puncture through the patient's skin and thereby draw a blood sample, and a retracted position (as illustrated in FIG. 5), at which to be completely surrounded and shielded by the outer protective sleeve 2. The needle 18 communicates with a conventional evacuated fluid (e.g. blood) collection tube 26 at the interior of the outer sleeve 2, so that the patient's blood sample can be safely stored and transported for subsequent study.

Extending outwardly from one side of needle carrier 18 is a position control button 28. Extending outwardly from another side of needle carrier 18 is a catch 30. As will soon be explained, position control button 28 and catch 30 are adapted to be received in and slide through the guide channel 10 and catch sot 16, respectively, of outer sleeve 2 for the important purposes of controlling the position of needle 8 relative to outer sleeve 2 and for automatically causing the needle to cant so that the needle may be destroyed and reuse thereof prevented after the last blood sample has been collected.

To this end, position control button 28 includes a relatively narrow stem 32 located between relatively wide and oppositely disposed shoulder and finger pad portions. A pair of short, parallel aligned, axially extending slots 34 are formed through needle carrier 18 at opposite sides of position control button 28 to permit button 28 to be rotated into the locking detents 12 and 14 of guide channel 10 so that button 28 may be moved through guide channel 10 to change the position of needle carrier 18 relative to outer sleeve 2. That is to say, a flexible locking spring 36 is established between axial slots 34 by which to normally bias the relatively wide shoulder portion of control button 28 into receipt by either the proximal or distal locking detent 12 or 14. As will soon be explained, the position control button can be depressed and, thereby, rotated into detent 12 or 14 to move the wide shoulder portion thereof out of said detent and permit the narrow stem 32 to slide through guide channel 10 so that the needle carrier 18 (and the needle 8 connected thereto) can be relocated from the proximal end towards the distal end of outer sleeve 2, or visa versa.

The catch 30 of inner needle carrier 18 projects outwardly from a tab 40 that is detachable from the side of the needle carrier. The tab 40 is coextensively connected to a portion 41 of the distal end of needle carrier 18 at which the hub 24 is connected and the needle 8 is retained. Distal end portion 41 is pivotally connected to the needle carrier 18 at the living hinge 42 (best shown in FIG. 3) formed at the distal aspect of the carrier. As will be described in greater detail when referring to FIGS. 4 and 5, the movement of catch 30 through the catch slot 16 controls the detachment of tab 40 from needle carrier 18 and the rotation of the distal end portion 41 around hinge 42, so that needle 8 can be canted toward the outer sleeve 2.

FIG. 4 of the drawings shows the syringe in an assembled configuration with the inner needle carrier 18 located within and moved axially through the outer protective sleeve 2, such that needle 8 is in an axially extended position. The position control button 28 is received through the distal locking detent (designated 14 in FIG. 1) and catch 30 is received in catch slot 16. Accordingly, the needle carrier 18 is locked at a relatively distal position within the outer sleeve 2. More particularly, the relatively wide shoulder of position control button 28 is located within locking detent 14. Therefore, position control button 28 is blocked from sliding proximally through guide channel 10, inasmuch as the diameter of the shoulder is larger than the width of the channel 10. Hence, the needle corner 18 is retained at the distal position with the needle 8 projecting outwardly through the distal opening 6 in outer sleeve 2 for making a veni puncture through the skin 44 of the patient.

An evacuated blood collection tube 26 is inserted through the open proximal end of outer sleeve 2 until the needle 8 penetrates a rubber stopper 46 of tube 26 so as to communicate with the interior thereof. Accordingly, one or more samples of the patient's blood may be automatically drawn into successive blood collection tubes 26 via needle 8. When the last blood sample has been taken, the needle 8 is withdrawn from the patient's skin 44 and the blood collection tube 26 is removed from outer sleeve 2, so that the blood sample can be centrifuged and studied.

Referring concurrently to FIGS. 1 and 5 of the drawings, the needle 8 is retracted and canted within the outer sleeve 2, so that syringe 1 may be safely discarded while preventing reuse of the needle and avoiding the potential for exposing a health care worker to an accidental needle strike. More particularly, the position control button 28 is depressed, whereby to cause locking spring 36 of needle carrier 18 to rotate inwardly and thereby locate the relatively narrow stem 32 of button 28 within the distal locking detent 14. Inasmuch as the diameter of stem 32 is less than the width of guide channel 10, the button 28 is now free to slide through channel 10. Manually sliding the button 28 axially and proximally through channel 10 causes inner needle carrier 18 to be moved proximally through outer sleeve 2, such that needle 18 is relocated from the axially extended position (of FIG. 4) to a retracted position. Moreover, the catch 30 of needle carrier 18 rides through catch slot 16.

As previously disclosed, the length of guide channel 10 is longer than the length of catch slot 16. Therefore, the proximal movement of position control button 28 through channel 10 will cause catch 30 to reach the end of catch slot 16 before button 28 is received in proximal locking detent 12. With catch 30 located at the end of catch slot 16, the continued proximal movements of position control button 28 toward distal locking detent 12 and needle carrier 18 through outer sleeve 2 automatically causes the tab 40, to which catch 30 is connected, to become detached from the side of carrier 18 and rotated around the hinge 42 (in the direction of reference arrow 48). Accordingly, the distal end portion 41 of needle carrier 18, at which the needle hub 24 is connected is correspondingly rotated, whereby to cant needle 8 relative to the longitudinal axis of syringe 1 and towards the outer sleeve 2.

When the position control button 28 is received and locked within distal locking detent 12, the distal end portion 41 of inner needle carrier 18 has been sufficiently rotated so that the needle 8 is moved into contact with and bent against the side of outer protective sleeve 2. Hence, the inner needle carrier 18 is locked at a proximal position relative to outer sleeve 2 with needle 8 safely retained at the retracted position and completely surrounded by outer sleeve 2 to avoid an accidental needle strike. Moreover, and by virtue of the present invention, the needle 8 is canted and bent to prevent access to and reuse of the needle. What is more, and unlike any known shielded safety syringe, the health care worker is also protected against an accidental needle strike via distal opening 6 in outer sleeve 2 in the event that the needle 8 should be inadvertently returned toward the axially extended position (of FIG. 4). That is to say, the canted orientation of needle 8 (i.e. out of alignment with opening 6) prevents the relocation of needle 8 from the retracted position of FIG. 5 to the extended position of FIG. 4. Thus, the canted and bent needle 8 acts as a redundant safety locking feature (along with the receipt of position control button 28 in proximal locking detent 12) which blocks the movement of needle 8 outwardly from outer sleeve 2 via the distal opening 6 thereof.

In view of the foregoing, a disposal cartridge is created (in FIG. 5) having the inner needle carrier 18 locked in a proximal position with needle 8 retained in a retracted position within outer sleeve 2. The needle 8 is canted, bent, surrounded, and shielded by the outer sleeve 2, so that syringe 1 may be safely handled while avoiding the possibility of a needle strike and the spread of a contagious and, possibly life threatening, disease.

It will be apparent that while a preferred embodiment of the invention has been shown and described, various modifications and changes may be made without departing from the true spirit and scope of the invention. Having thus set forth a preferred embodiment of the invention, what is claimed is:

We claim:

1. A syringe comprising an outer protective sleeve having proximal and distal ends and comprising:
    needle carrying means located within and movable axially through said outer sleeve;
    a double-ended hypodermic needle retained by said needle carrying means and movable therewith, one end of said needle aligned to communicate with a fluid collection tube at the interior of said outer sleeve and the second end of said needle located at either an axially extended position projecting outwardly and past the distal end of said outer sleeve or a retracted position completely surrounded and shielded by said outer sleeve, depending upon the location of said needle carrying means relative to said outer sleeve; and
    means interconnected between said needle and said needle carrying means around which said needle may rotate within said outer sleeve for canting said needle relative to the longitudinal axis of said outer sleeve when the second end of said needle is located at the retracted position.

2. The syringe recited in claim 1, further comprising a guide channel formed in and extending between the proximal and distal ends of said outer sleeve and a position control button extending from said needle carrying means to be received in and slideable through said guide channel for moving said needle carrying means axially through said outer sleeve.

3. The syringe recited in claim 2, wherein said guide channel has proximal and distal locking detents located at opposite ends thereof for receiving said position control button and thereby retaining said second end of said needle at either the axially extended position or the retracted position, respectively.

4. The syringe recited in claim 1, wherein said needle carrying means has an open proximal end and a substantially closed distal end, said needle being retained at the distal end of said needle carrying means, said needle canting means including at least a portion of said distal end at which said needle is retained, said distal end portion being pivotally connected to said needle carrying means.

5. The syringe recited in claim 4, wherein one end of said distal end portion is hingedly connected to said needle carrying means and the opposite end of said distal end portion is detachably connected to said needle carrying means, such that said distal end portion at which said needle is retained is rotatable towards said outer sleeve.

6. The syringe recited in claim 4, further comprising a catch extending from said distal end portion and a catch slot formed in said outer sleeve, said catch being received in and slideable through said catch slot when said needle carrying means moves axially through said outer sleeve.

7. A syringe comprising:
    an outer protective sleeve having an open proximal end and a substantially closed distal end;
    needle carrying means located within and movable axially through said outer sleeve, said needle carrying means having an open proximal end and a substantially closed distal end; and
    a double-ended hypodermic needle retained by said needle carrying means at the distal end thereof and moveable with said needle carrying means through said outer sleeve, one end of said needle communicating with a fluid collection tube at the interior of said outer sleeve and the second end of said needle being retractable from an axially extended position projecting outwardly and past the distal end of said outer sleeve to a retracted position completely surrounded and shielded by said outer sleeve;

at least a portion of the distal end of said needle carrying means at which said needle is retained being pivotally connected to said needle carrying means so that said distal end portion may be rotated and said needle canted toward said outer sleeve when said needle is relocated to the retracted position.

8. The syringe recited in claim 7, further comprising:
a position control button extending from said needle carrying means;
a catch extending from the rotatable distal end portion of said needle carrying means at which said needle is retained;
guide channel means formed in said outer sleeve between the proximal and distal ends thereof, said position control button being received in and slideable through said guide channel means for moving said needle carrying means through said outer sleeve and thereby relocating said needle between the axially extended and retracted positions; and
catch slot means formed in said outer sleeve in parallel alignment with said guide channel means, said catch being received in and slideable through said catch slot means when said needle carrying means is moved through said outer sleeve.

9. The syringe recited in claim 8, wherein said guide channel means is of longer length than said catch slot means.

10. The syringe recited in claim 7, wherein one end of the rotatable distal end portion of said needle carrying means is detachably connected to said needle carrying means and the opposite end thereof is hingedly connected to said needle carrying means.

11. The syringe recited in claim 7, wherein said fluid collection tube is an evacuated blood collection tube.

12. A syringe comprising an outer cylinder, a needle carrier movable axially through said outer cylinder, and a hypodermic needle retained by said needle carrier and movable therewith through said cylinder such that said needle can be advanced to a first position, at which said needle projects outwardly from said cylinder so that a fluid may be supplied via said needle to the interior of said cylinder, or said needle can be retracted to a second position, at which said needle is surrounded and shielded by said cylinder to prevent an accidental needle strike, said needle being hingedly interconnected with said needle carrier so as to be rotatable with respect to said needle carrier and thereby canted relative to the longitudinal axis of said outer cylinder when said needle is located at the second, retracted position surrounded by said cylinder.

13. The syringe recited in claim 12, further comprising means to anchor said needle at the second, retracted position within said outer cylinder after said needle has been rotated and canted to prevent a relocation of said needle to the first, outwardly projecting position.

14. The syringe recited in claim 12, further comprising a guide channel formed in and extending axially through said outer cylinder and a position control button extending from said needle carrier to be received in and slideable through said guide channel for moving said needle carrier axially through said outer cylinder and for correspondingly moving said needle from the first to the second position.

15. The syringe recited in claim 14, wherein said guide channel has first and second locking detents located at opposite ends thereof for receiving said position control button and thereby retaining said needle at either the first, outwardly projecting position of the second, retracted position, respectively, depending upon the location of said needle carrier relative to said outer cylinder.

16. The syringe recited in claim 14, further comprising a catch extending outwardly from said needle carrier and a catch slot formed in and extending axially through said outer cylinder, said catch being received in and slideable through said catch slot when said needle carrier moves through said outer cylinder, said guide channel being of longer length than said catch slot.

17. The syringe recited in claim 16, further comprising hinge means interconnected between said needle carrier and said needle around which said needle is rotated and canted when the position control button of said needle carrier moves through said guide channel a greater distance than the distance moved by the catch of said needle carrier through said catch slot.

18. The syringe recited in claim 17, wherein said needle carrier commprises first and second ends pivotally connected to one another, said first end having said position control button extending therefrom and said second end retaining said needle and having said catch extending therefrom, said hinge means interconnected between the first and second ends of said needle carrier so that said second end is rotatable relative to said first end around said hinge means for canting said needle when the position control button of said first end moves through said guide channel a greater distance than the distance moved by the catch of said second end through said catch slot.

19. The syringe recited in claim 12, wherein said needle carrier comprises first and second ends pivotally interconnected with one another, said second end retaining said needle thereat, and said syringe further comprising hinge means located between the first and second ends of said needle carrier, such that said second end is rotatable relative to said first end around said hinge means for canting the needle relative to the longitudinal axis of said outer cylinder.

20. The syringe recited in claim 12, wherein said outer cylinder has an open end to receive a blood collection tube therewithin and said hypodermic needle is double ended, one end of said needle extending into said cylinder and aligned to be in fluid communication with the blood collection tube when said tube is received by said cylinder, the opposite end of said needle being movable between said first and second positions, depending upon the location of said needle carrier to said cylinder.

* * * * *